US 6,915,901 B2

(12) United States Patent
Feinberg et al.

(10) Patent No.: US 6,915,901 B2
(45) Date of Patent: Jul. 12, 2005

(54) PACKAGING ASSEMBLY FOR SURGICAL USE

(76) Inventors: Marc Feinberg, 17 Becks Blvd., Ringoes, NJ (US) 08551; Mike Pohle, 15 Chestnut Trail, Flemington, NJ (US) 08822; Robin Peters, 24 Kershaw Ct., Bridgewater, NJ (US) 08807; Lance Stairs, 6 Nicole La., Flemington, NJ (US) 08822; Tucker H. Fort, 571 Hudson St., #6A, New York, NY (US) 10014; Richard Whitehall, 323 E. 8$^{th}$ St., #2A, New York, NY (US) 10009

( * ) Notice: Subject to any disclaimer, the term of this patent is extended or adjusted under 35 U.S.C. 154(b) by 30 days.

(21) Appl. No.: 10/016,240

(22) Filed: Dec. 10, 2001

(65) Prior Publication Data

US 2002/0108875 A1 Aug. 15, 2002

Related U.S. Application Data

(60) Provisional application No. 60/254,682, filed on Dec. 11, 2000.

(51) Int. Cl.$^7$ .......................... B65D 83/10; B65D 69/00; B65D 73/00; A61B 17/06
(52) U.S. Cl. ....................... 206/363; 206/438; 206/471; 206/477; 206/570
(58) Field of Search ................................. 206/363–365, 206/63.3, 63.5, 219, 221, 438, 439, 564, 223, 570–572, 443, 471, 277, 377, 378, 486, 477; D24/227, 229; 606/214

(56) References Cited

U.S. PATENT DOCUMENTS

| | | | |
|---|---|---|---|
| 1,367,600 A | 2/1921 | Hirsch | |
| 1,446,741 A | 2/1923 | Faber | |
| 2,025,522 A | 12/1935 | Myers | |
| 2,224,027 A | 12/1940 | Tate | |
| 2,944,665 A | 7/1960 | Obeck | |
| 2,974,782 A | 3/1961 | Walters | |
| 3,058,584 A | 10/1962 | Marshall | |
| 3,153,531 A | 10/1964 | Cook | |
| 3,248,017 A | 4/1966 | Allen | |
| 3,497,982 A | 3/1970 | Schulz | |
| 3,698,551 A | 10/1972 | Tomlinson | |
| 3,927,762 A | 12/1975 | Zdarsky et al. | |
| 3,951,261 A | 4/1976 | Mandel et al. | |
| 3,951,263 A | 4/1976 | Vale | |
| 4,023,678 A | 5/1977 | Fiedler | |
| 4,091,927 A | 5/1978 | Lunsford | |
| 4,412,617 A | * 11/1983 | Cerwin ..................... 206/339 | |
| 4,424,898 A | 1/1984 | Thyen et al. | |
| 4,482,053 A | * 11/1984 | Alpern et al. ............... 206/439 | |
| 4,619,364 A | 10/1986 | Czopor, Jr. | |
| 4,736,850 A | 4/1988 | Bowman et al. | |
| 4,915,233 A | 4/1990 | Smith | |
| 5,024,323 A | 6/1991 | Bolton | |
| 5,099,994 A | 3/1992 | Kalinski et al. | |
| 5,199,567 A | * 4/1993 | Discko, Jr. ................. 206/369 | |
| 5,322,163 A | 6/1994 | Foos | |
| 5,323,907 A | 6/1994 | Kalvelage | |
| 5,351,822 A | 10/1994 | Sinn | |
| 5,353,922 A | 10/1994 | Sinn | |
| 5,358,116 A | 10/1994 | Brintazzoli | |
| 5,361,907 A | 11/1994 | Mohrhauser | |
| 5,375,717 A | 12/1994 | Roshdy | |
| 5,379,895 A | * 1/1995 | Foslien ..................... 206/363 | |
| 5,386,908 A | * 2/1995 | Sinn ......................... 206/363 | |
| 5,392,919 A | 2/1995 | Passamoni | |

(Continued)

Primary Examiner—Mickey Yu
Assistant Examiner—J. Gregory Pickett

(57) ABSTRACT

A package assembly holds at least one applicator nozzle tip and, optionally, a fluid-containing vial adapted for attachment to the nozzle tip. By providing the vial with a fluid-dispensing end, it may be used with or without the nozzle tip. When used in combination, the vial and nozzle tip can be employed to dispense, for instance, a medical adhesive to a wound site.

8 Claims, 12 Drawing Sheets

U.S. PATENT DOCUMENTS

| | | |
|---|---|---|
| 5,477,964 A | 12/1995 | Hart |
| 5,485,917 A * | 1/1996 | Early ......................... 206/363 |
| 5,485,919 A | 1/1996 | Samberg et al. |
| 5,544,755 A | 8/1996 | Paumen et al. |
| 5,575,382 A | 11/1996 | Sobel et al. |
| 5,577,606 A | 11/1996 | Schwentuchowski et al. |
| RE35,445 E | 2/1997 | Pora |
| 5,617,952 A | 4/1997 | Kranendonk |
| 5,699,909 A | 12/1997 | Foster |
| 5,704,469 A | 1/1998 | Daniele et al. |
| 5,788,062 A | 8/1998 | Cerwin et al. |
| 5,788,063 A | 8/1998 | Van Ness |
| 5,833,099 A * | 11/1998 | Boaz et al. ................. 222/568 |
| 5,928,611 A | 7/1999 | Leung |
| 5,947,284 A * | 9/1999 | Foster ......................... 206/364 |
| 6,047,826 A * | 4/2000 | Kalinski et al. ............ 206/365 |
| 6,170,663 B1 | 1/2001 | Glassman |
| 6,346,109 B1 | 2/2002 | Fucci et al. |
| 6,394,269 B1 | 5/2002 | Rudnick et al. |
| 6,412,639 B1 | 7/2002 | Hickey et al. |
| 6,425,704 B2 | 7/2002 | Voiers et al. |
| 6,439,789 B1 | 8/2002 | Ballance et al. |
| 6,458,095 B1 | 10/2002 | Wirt et al. |
| 2001/0031170 A1 | 10/2001 | Voiers et al. |
| 2002/0176732 A1 | 11/2002 | Quintero et al. |

* cited by examiner

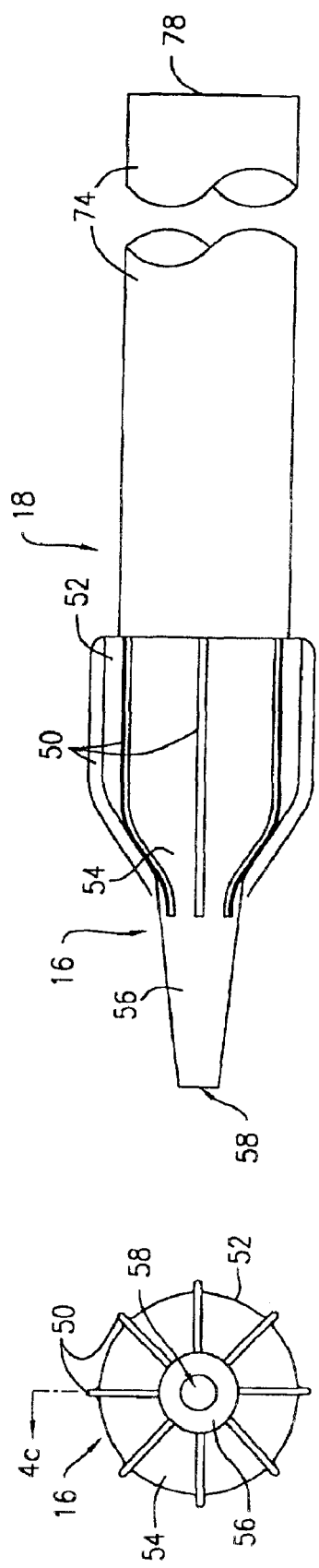

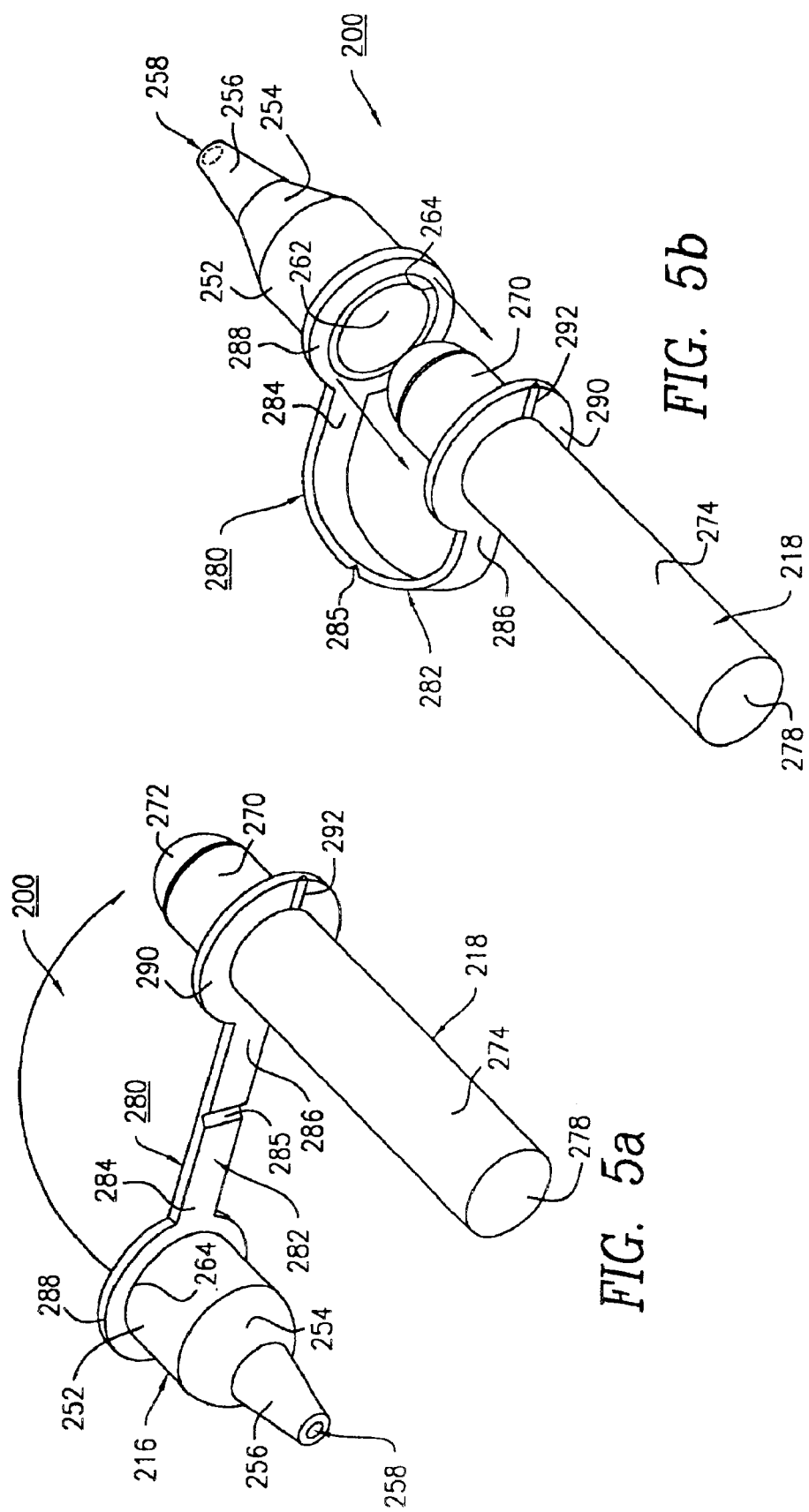

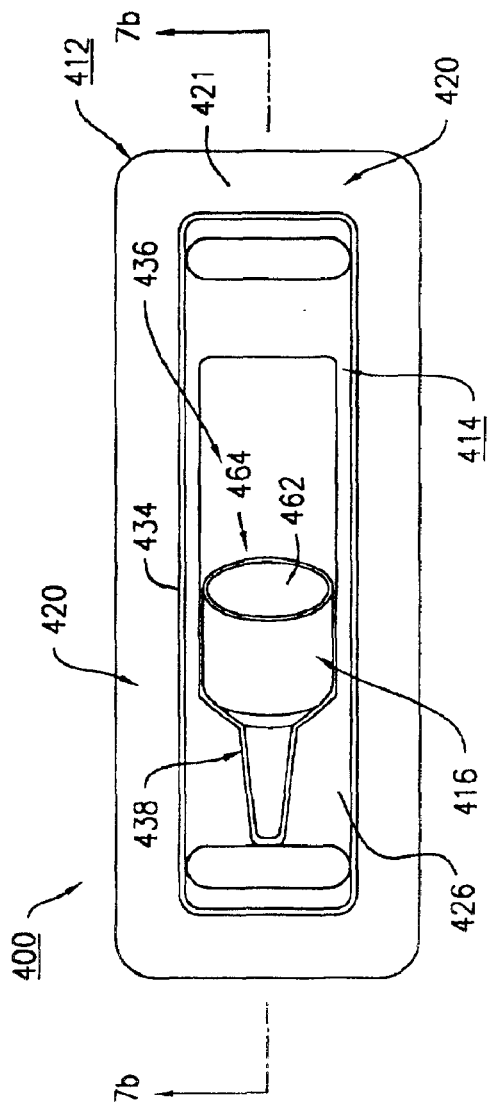
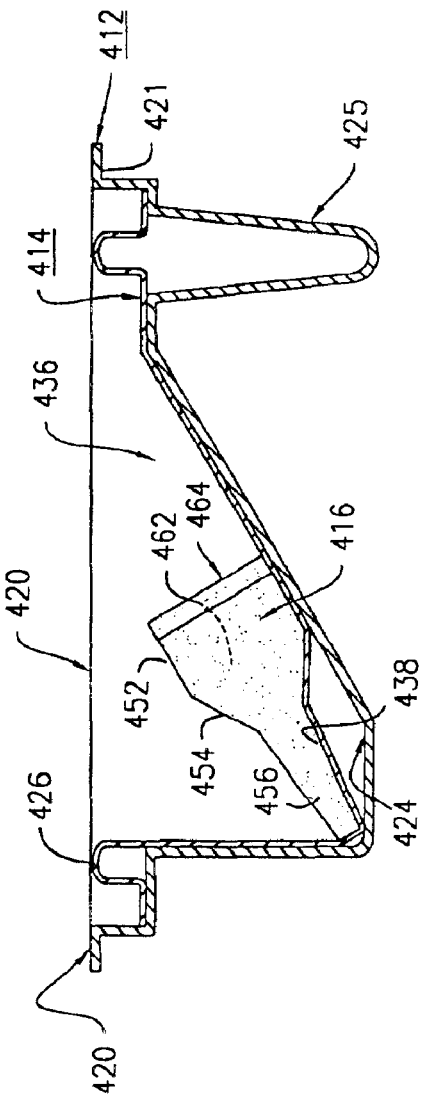
FIG. 7a
FIG. 7b

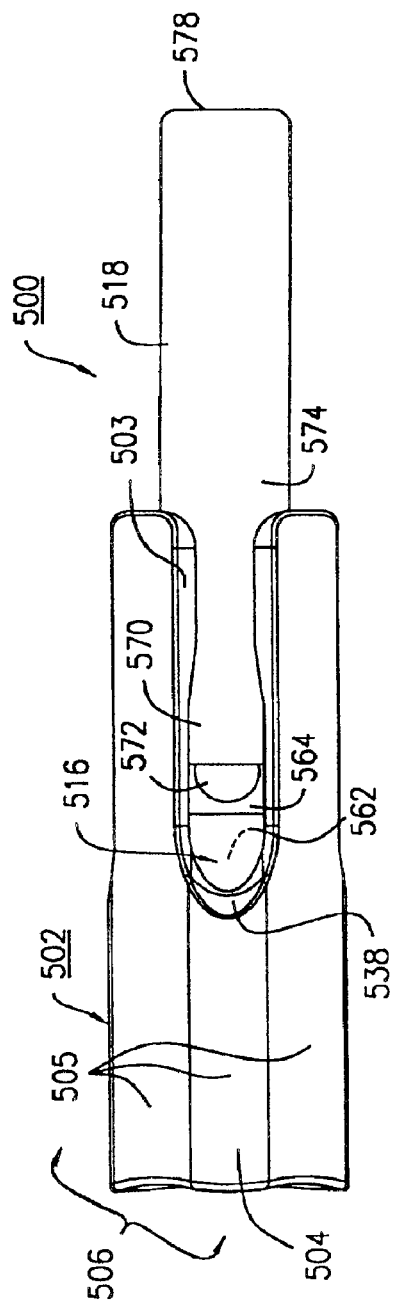
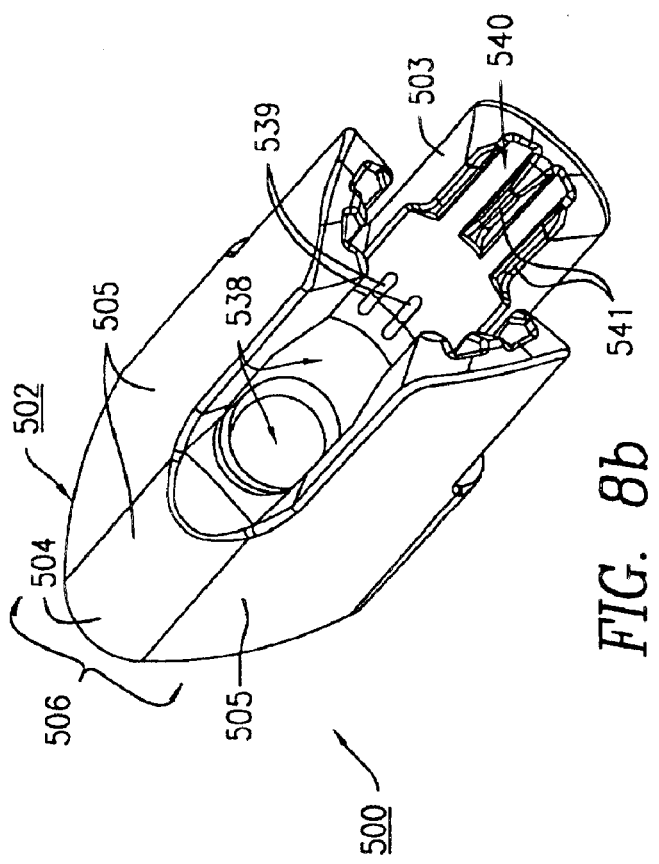

PACKAGING ASSEMBLY FOR SURGICAL USE

CROSS REFERENCE TO RELATED APPLICATION

This is a §111(a) application relating to Provisional U.S. Application Ser. No. 60/254,682 filed Dec. 11, 2000.

FIELD OF THE INVENTION

The present invention relates to packaging and dispensing apparatus for adhesives and, more particularly, to such packaging and dispensing apparatus which are especially adapted for use in surgical and other medical applications.

BACKGROUND OF THE INVENTION

Medical/surgical adhesives are well known in the medical art. Examples of such medical adhesives include DERMABOND™, a topical skin adhesive, and HISTOCRYL™, a cryanoacrylate adhesive. Typically, the medical adhesive is dispensed from a product vial through an applicator nozzle tip onto a patient's wound or surgical area. Many of the medical adhesives are based on liquid cryanoacrylate formulations, and most of these liquid adhesives are packaged in cylindrically-shaped vials. Some of these product vials have porous end caps for dispensing of the medical adhesives to the wound area. Other adhesive product vials have applicator nozzle tips thereon for directing the application of the medical adhesive to a localized area on the wound.

As often happens in surgery, the surgeon has no way of knowing the exact shape of the patient's (wound) tissue surfaces on which the medical adhesives will be required. Accordingly, surgeons typically request that a variety of medical adhesive materials be made available during a single surgical procedure on the patient's wound. Some of these medical adhesive materials are suitable for broad stroke application on the wound area via the adhesive product vial. Other medical adhesive product vials have special applicator nozzle tips for pin-point application to a specific wound area on the patient. In this typical surgical condition, there are multiple adhesive product vials at the surgical site which take up the limited sterile surgical site area that is available. Further, since the adhesive product vials are typically cylindrically-shaped, these product vials have a tendency to roll-off the sterile surgical field and become contaminated (unusable by the surgeon) in an unsterile area (i.e., the floor). Alternatively, single porous adhesive product (vial) applicators may be placed in the sterile field along with separate packages of various applicator nozzle tips to remedy the previous surgical situation. Although this solution sounds reasonable, the approach adds to the number of adhesive product vials, the secondary packages of applicator nozzle tips and further (additional) clutter in the sterile field. Additionally, the applicator nozzle tips are small in size and therefore may be easily lost in the sterile field by the surgeon.

In the foregoing circumstances, there remains a need for a packaging assembly for surgical use having a single adhesive product vial that is capable of administering the medical adhesive in broad strokes to a patient's wound and/or having the adhesive product vial modified with an applicator nozzle tip prior to use for a more precise application of the medical adhesive. Additionally, there is a need for an adhesive product vial that may be placed in the sterile field without the surgeon's concern that the adhesive product vial will roll-off and out of the sterile field. Still further, there remains a need for a convenient way to modify an adhesive product vial in order to provide a different type of an applicator nozzle tip from the standard one that is normally affixed to the vial.

DESCRIPTION OF RELATED ART

U.S. Pat. No. 5,928,611 to Leung discloses an impregnated applicator nozzle tip containing a polymerization and/or cross-linking initiator. The applicator nozzle tip may be detachable from the product container holding the polymerization and/or cross-linkable material therein. The applicator nozzle tip can be attached to the container prior to use and detached from the container subsequent to use in order to prevent premature polymerization or cross-linking of the unapplied adhesive material in the container. The applicator nozzle tip may be discarded after its initial use and a new applicator nozzle tip may be attached to the product container for subsequent use. Alternatively, the initially used nozzle tip may be reattached to the product container and used again.

In the foregoing circumstances, it is an object of the present invention to provide a packaging assembly that facilitates a final assembly of its product components prior to their removal from the packaging assembly.

Another object of the present invention is to provide a packaging assembly having a single adhesive product vial which is capable for use in applying broad strokes of adhesive or which can be modified immediately prior to use for a more precise application of the adhesive product.

An additional object of the present invention is to provide a secondary applicator nozzle tip for attachment onto a porous tipped end cap of an adhesive product vial.

A further object of the present invention is to provide an adhesive product vial that may be placed in a sterile field without the concern of the product vial rolling off and out of the sterile field.

The present invention also has the objective of providing a packaging assembly that can conveniently modify an adhesive product vial through the use of removable interchangeable application nozzle tips.

A still further object of the present invention is to provide a packaging assembly that can be used for guiding, aligning and/or positioning a secondary applicator nozzle tip onto the porous applicator end cap of the adhesive product vial.

The present invention has the further objective of providing an applicator nozzle tip with a plurality of reinforcing ribs for increasing the structural strength and rigidity of the nozzle tip, while aiding the removal of the nozzle tip from the packaging assembly.

Yet another object of the present invention is to provide an applicator nozzle tip that includes a series of internal rings for maintaining a leak-resistant seal between the nozzle tip and the adhesive vial attached thereto.

Yet still another object of the present invention is to provide an applicator nozzle tip that includes an internal chamber which serves to align the applicator nozzle tip with that of the porous applicator end cap of the surgical adhesive product vial.

SUMMARY OF THE INVENTION

The present invention overcomes the disadvantages of the prior art discussed above and achieves the aforementioned objectives, by providing a package assembly which is adapted to hold an applicator nozzle tip such that it is positioned for ready and easy attachment to a fluid-containing vial without removing the nozzle tip from the package assembly. In one exemplary embodiment, the package assembly holds both the nozzle tip and the vial such that they can be attached prior to their removal from the package assembly. Once attached, the resulting combination may include the following components: a vial having medical adhesive therein and a porous dispensing end; and an initially empty nozzle tip removably attached to the vial over the porous dispensing end thereof.

BRIEF DESCRIPTION OF THE DRAWINGS

Further objects, features and advantages of the present invention will become apparent upon consideration of the following detailed description of various exemplary embodiments considered in connection with the accompanying drawings, in which:

FIG. 4a is a distal end view of the applicator nozzle tip of FIG. 3a;

FIG. 4b is a side elevational view of the applicator nozzle tip and its attached product vial of FIGS. 1 and 2;

FIG. 4c is a cross-sectional view, taken along section line 4c—4c and looking in the direction of the arrows, of the applicator nozzle tip of FIG. 4a;

FIG. 4d is a cross-sectional view, taken along section line 4c—4c and looking in the direction of the arrows, of the applicator nozzle tip and the product vial of FIG. 4a;

FIG. 5a is a perspective view of an alternative detachable applicator nozzle tip and its connected product vial constructed in accordance with a third exemplary embodiment of the present invention;

FIG. 5b is a perspective view similar to FIG. 5a except that the applicator nozzle tip is shown just prior to its attachment to the distal end of the product vial;

FIG. 6b is an exploded perspective view of the surgical adhesive package of FIG. 6a;

FIG. 7a is a top plan view of a package assembly constructed in accordance with a fifth exemplary embodiment of the present invention showing only a single nozzle tip therein;

FIG. 7b is a cross-sectional view, taken along section line 7b—7b and looking in the direction of the arrows, of the package assembly and the nozzle tip of FIG. 7a;

FIG. 8a is a top view of a surgical adhesive package assembly constructed in accordance with a sixth exemplary embodiment of the present invention;

FIG. 8b is a rear perspective view of the adhesive package assembly of FIG. 8a showing its tri-lobe configuration;

FIG. 9b is a rear perspective view of the adhesive package assembly of FIG. 9a;

DETAILED DESCRIPTION OF THE EXEMPLARY EMBODIMENTS

First Exemplary Embodiment 10

Figure 1:
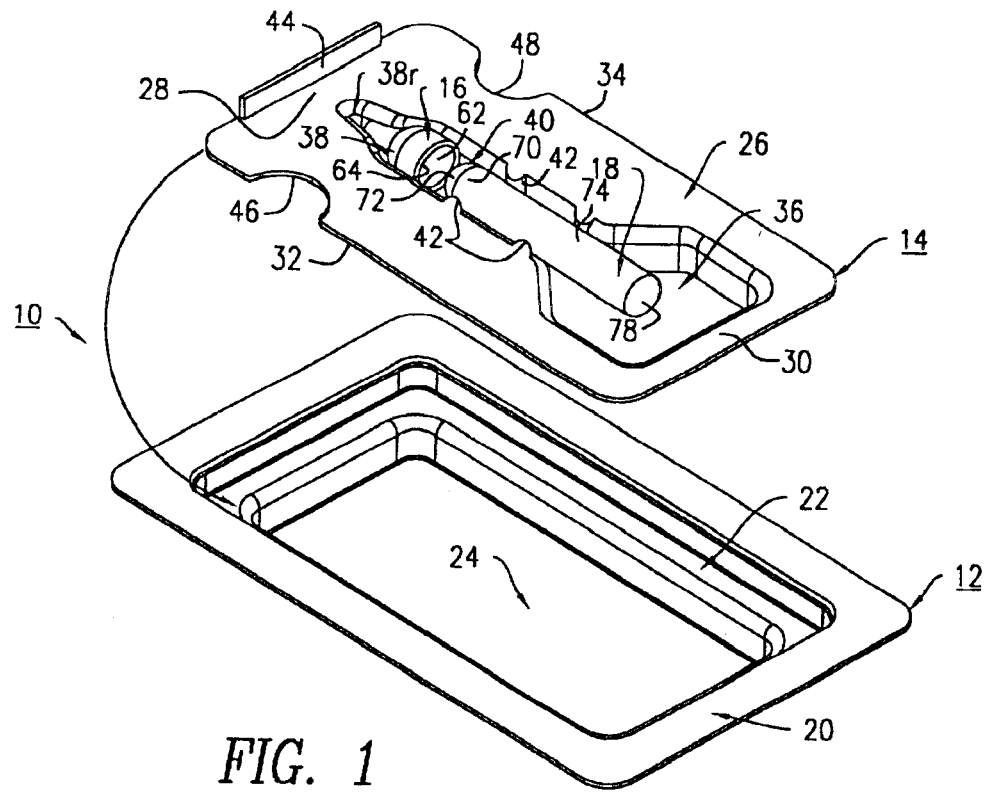
FIG. 1 is an exploded perspective view of a surgical adhesive package assembly constructed in accordance with a first exemplary embodiment of the present invention.

Referring to FIGS. 1, 3a, 3b, 4a to 4d, there is shown a surgical adhesive package assembly/kit 10 constructed in accordance with a first embodiment of the present invention. The surgical adhesive package assembly 10 includes a thermoformed, blister-type package outer tray 12, a thermoformed, blister-type package inner tray 14, an applicator nozzle tip 16 and an adhesive product vial 18. The product vial 18 contains a surgical/medical adhesive such as a DERMABOND™ topical skin adhesive or a HISTOCRYL™ cryanoacrylate adhesive for use during surgical procedures on a patient. The inner tray 14 facilitates a final assembly of product components 16 and 18 prior to their removal from the inner tray 14. Additionally, the package assembly 10 contains a single adhesive product that is capable for use in applying broad strokes of adhesive to the treatment area, or the adhesive product and the nozzle tip is modified immediately prior to use for more precise applications of the adhesive.

The outer tray 12 includes an outer perimeter rim 20, an inner perimeter ledge 22 for receiving the inner tray 14 thereon, and an interior compartment 24 (see FIG. 1). The inner tray 14 includes a planar wall surface 26 having a distal end 28, a proximal end 30, and side edges 32, 34. The planar wall surface 26 further includes a centrally located interior cavity 36 therein, as shown in FIG. 1. The interior cavity 36 is sized and shaped to separately hold the applicator nozzle tip 16 within a nozzle cavity section 38 and the adhesive product vial 18 within a vial cavity section 40. The interior cavity 36 of the inner tray 14 is cooperatively received within the interior compartment 24 of the outer tray 12. The interior cavity 36 also includes a plurality of holding tabs 42 adapted to hold the product vial 18 in place (see FIG. 1). The nozzle tip 16 and the product vial 18 are aligned along their longitudinal axes within the adjacent nozzle and vial sections 38, 40 of interior cavity 36. The holding tabs 42 allow the nozzle tip 16 and the product vial 18 to be movably secured along the length of the nozzle and vial sections 38, 40 of the interior cavity 36. The nozzle tip 16 and the product vial 18 are secured so as to resist movement during normal handling of the package assembly 10, but not too secure as to resist movement (either longitudinally or for removal) until the intervention of an operator. The distal end 28 of planar wall surface 26 includes a lifting tab 44 for lifting the inner tray 14 from the inner perimeter ledge 22 of the outer tray 12. The side edges 32, 34 of the planar wall surface 26 include finger grips 46, 48, respectively, each of which is positioned towards and adjacent to the distal end 28 of the planar wall surface 26. The finger grips 46, 48 are sized and shaped for gripping by the fingers of the operator such that the operator can grip the inner tray with one hand while advancing the adhesive product vial 18 into the applicator nozzle tip 16 with the other hand.

Figure 3A:
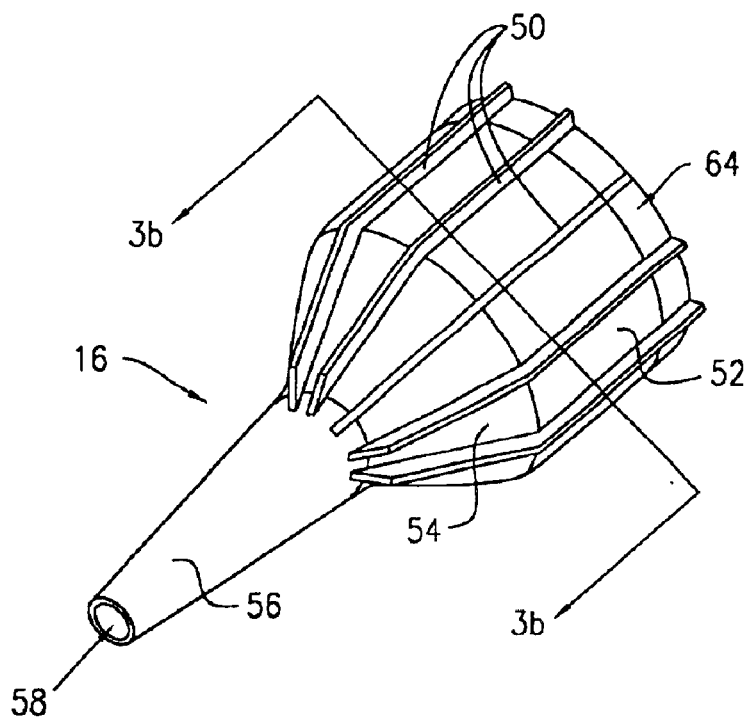
FIG. 3a is a front perspective view of an applicator nozzle tip used in the package assembly illustrated in FIGS. 1 and 2.
Figure 3B:
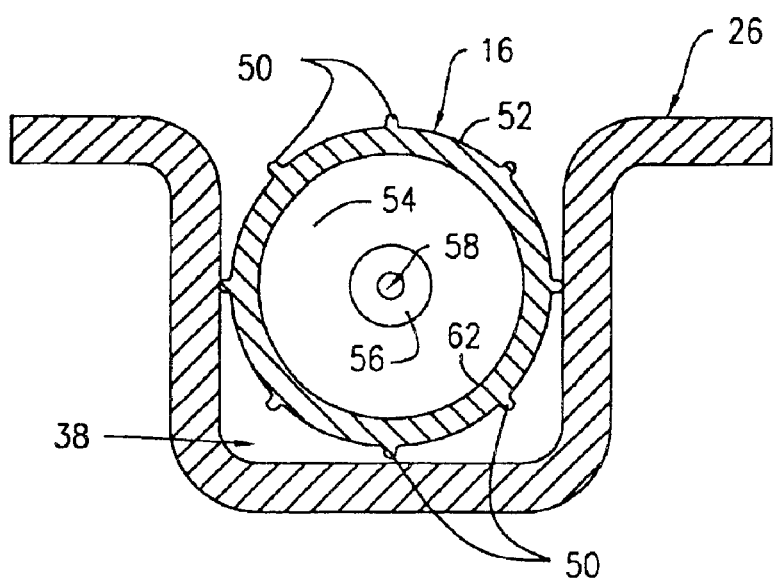
FIG. 3b is a cross-sectional view, taken along section line 3b—3b and looking in the direction of the arrows, of the applicator nozzle tip of FIG. 3a showing the nozzle tip positioned in a cavity within the adhesive package.

Referring now to FIGS. 3a, 3b and 4a to 4d, the applicator nozzle tip 16 includes a plurality of longitudinal ribs 50 equally spaced on an outer cylindrical wall section 52 and on a corresponding beveled/angled wall section 54. The nozzle tip 16 also includes a conical section (distal end) 56 having a tip opening 58 therein for extruding the adhesive material contained in the product vial 18. The ribs 50 have two advantages in reference to the structure of nozzle tip 16. One advantage, as shown in FIG. 3b, is to provide additional traction for holding the nozzle tip 16 in place within the nozzle section 38 of the interior cavity 36. The second advantage is that the ribs 50 improve the stiffness (i.e., rigidity) of the nozzle tip 16. This added stiffness serves to resist unwanted nozzle deformation either during assembly with the product vial 18 and/or during use when applying the tissue/surgical adhesive in the course of a medical procedure. To further aid in securing the nozzle tip 16 onto the product vial 18, the nozzle tip 16 includes a series of circumferential rings 60 (see FIGS. 4c and 4d) on an inner/interior wall surface 62 adjacent to a proximal end section 64 of the nozzle tip 16. The inner wall surface 62 further includes a beveled inner wall surface 66 that further aids in guiding the product vial 18 as it is inserted into the proximal end section 64 of the nozzle tip 16. The rings 60 may be molded integrally to the inner wall surface 62 of nozzle tip 16 or may be separate rings (e.g., "O" rings that are added later). In addition to securely attaching the nozzle tip 16 to the product vial 18, the rings 60 also serve to provide additional structural strength to the nozzle tip 16. The inner geometry (beveled wall surface 66) of the proximal end section 64 is designed so that the nozzle tip 16 will snap into place on the product vial 18, thereby resisting inadvertent separation of the nozzle tip 16 from the product vial 18. A further advantage of assembling the nozzle tip 16 onto the product vial 18 just before use is that the nozzle material will provide a sufficiently secure fit, without the risk of material relaxation causing leakage because the tip is not under stress during its shelf life.

Referring again to FIGS. 1, 4b and 4d, the adhesive vial product 18 is in the form of a cylindrically-shaped container and includes a distal end 70 having a porous end cap 72 thereon, an outer container wall 74, an inner cavity area 76 (i.e., in the form of an ampoule containing the medical adhesive material therein) and a proximal end 78. The porous end cap 72 allows the adhesive material to pass therethrough. As described above, the nozzle tip 16 is securely fitted onto the porous end cap 72 of the product vial 18 when the surgical wound requires a finer application of adhesive to be applied. In situations in which a broad application of adhesive is desired, the nozzle tip 16 can be omitted from the product vial, whereby the adhesive would be applied to the patient's wound via the porous end cap 72.

Figure 2:
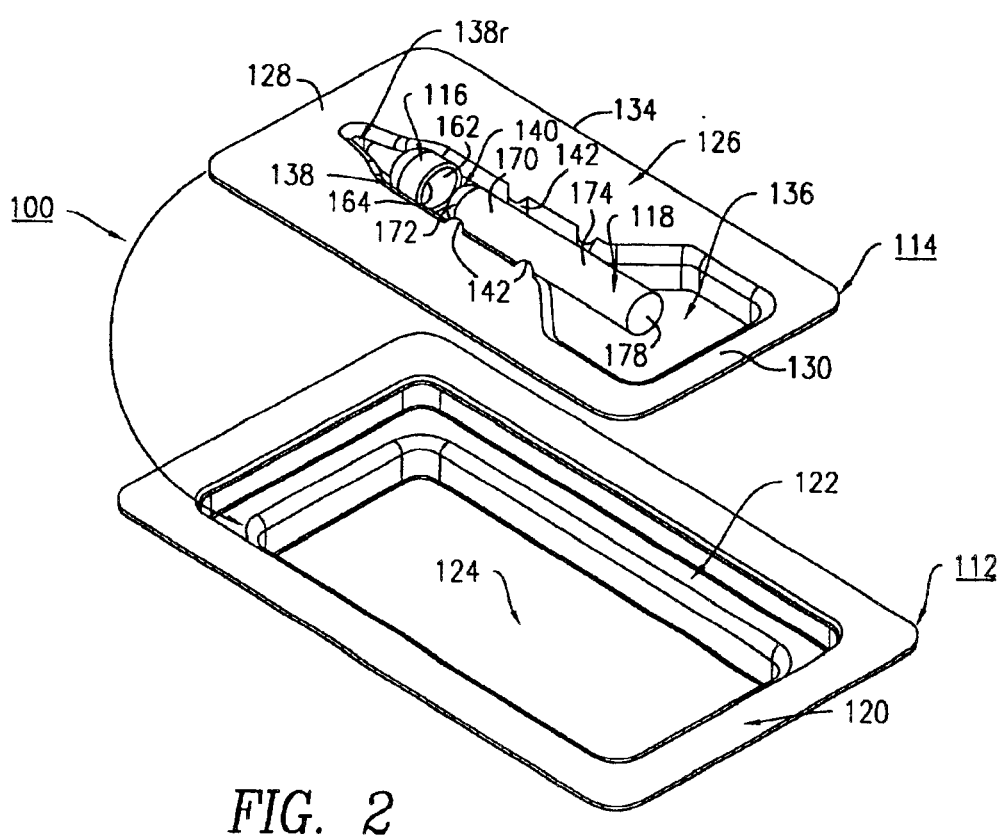
FIG. 2 is an exploded perspective view of a surgical adhesive package assembly constructed in accordance with a second exemplary embodiment of the present invention.

The trays 12, 14 of the package assembly 10 may be fabricated from any suitable material for medical or surgical packaging. The trays 12, 14 of package assembly 10 may be either transparent, translucent, opaque or any combination of these. Further, the trays 12, 14 of package assembly 10 may also include graphics and/or indicia for aiding the user in the use and/or identification of the product adhesive material. Additionally, the trays 12, 14 of package assembly 10 may be made of one or more components that are either thermoformed or injection molded. If injection molded, the overall design would be slightly different than what is shown in FIGS. 1 and 2 to accommodate well known considerations in the design of molded components. The applicator nozzle tip 16 and the adhesive product vial 18 are enclosed within the inner and outer trays 14, 12 of the package assembly 10 by a suitable barrier (such as a packaging lid made from TYVEK™ material) to assure product sterility. The packaging lid (not shown) is an example of such a barrier and in combination with the outer tray 12 may be referred to as secondary packaging. The packaging lid, which may be heat sealed to the outer perimeter rim 20 of the outer tray 12, could be provided with graphics and/or indicia for aiding the user in the use and/or identification of the adhesive material.

Figure 4C:
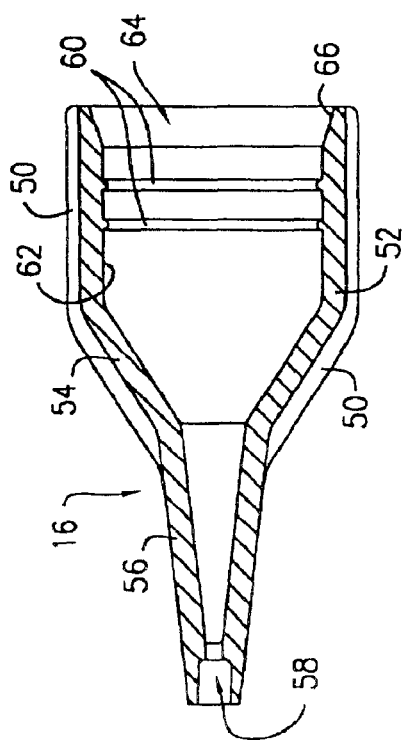
Figure 4D:
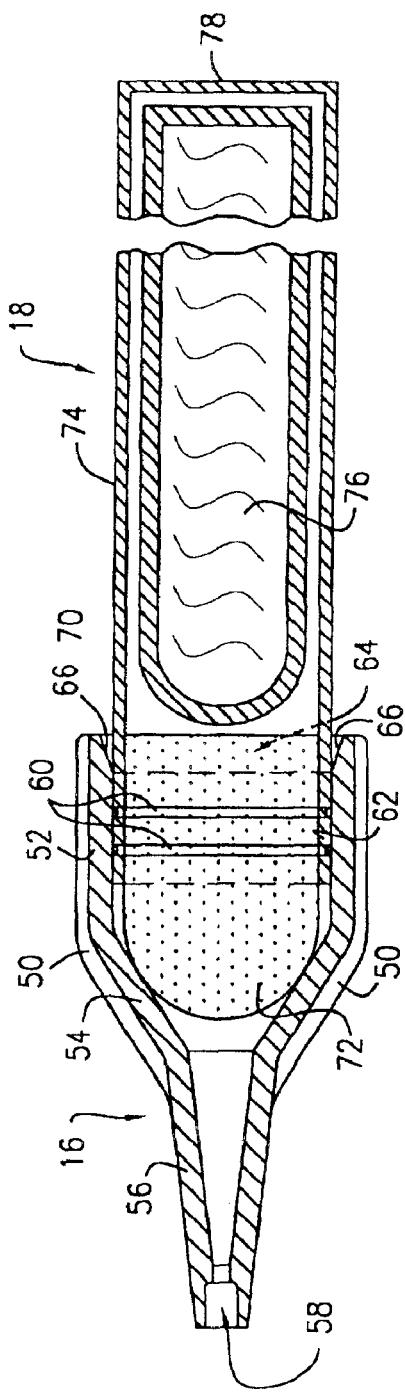

The design and operation of the surgical adhesive package assembly 10 lends itself for use where a sterile field or sterile area is desired. With reference to FIG. 1, the packaging assembly 10 operates in the following manner. First, the user or operator would remove the packaging lid (not shown) from the outer perimeter rim 20 of outer tray 12 in order to expose and free the inner tray 14. This would be done while the operator is in the vicinity of the sterile operating field. The operator then flips and turns over the inner tray 14 onto a surgical tray (not shown) within the sterile field. During this step, the applicator nozzle tip 16 and the adhesive product vial 18 remain substantially in their original positions within the inner tray 14, as depicted in FIG. 1. Since the inner tray 14 does not have a cylindrical or round shape, it will not roll around once positioned within the sterile field. The operator can then choose to remove the product vial 18 from the vial cavity section 40 of inner tray 14, while leaving the nozzle tip 16 in place in the nozzle cavity section 38. The operator can then use the product vial 18 (without the nozzle tip 16) for a broad application of adhesive on the patient's wound via the porous end cap 72. If the surgical wound requires a more precise and finer application of the adhesive, the operator can then choose to attach and connect the nozzle tip 16 to the porous end cap 72 of the product vial 18, as depicted in FIGS. 4b and 4d.

To apply the applicator nozzle tip 16 to the porous end cap 72 of the product vial 18, the operator places his/her fingers (not shown) within the finger grips 46, 48 of inner tray 14 and then advances the porous end cap 72 of the product vial 18 forward to join and connect with the nozzle tip 16, which is positioned within the nozzle cavity section 38 of inner tray 14. It should be noted that the distal end 28 of the nozzle cavity section 38 is formed in a shape that will support the nozzle tip 16 and that will also protect the tip opening 58 by providing a small recess area 38r within the nozzle cavity section 38 just distal to the nozzle tip opening 58. The nozzle cavity section 38 supports the applicator nozzle tip 16 along the nozzle's exterior surfaces (i.e., the surfaces 52, 54 and 56) in order to allow the operator to insert the porous end cap 72 of the product vial 18 into the proximal end section 64 of nozzle tip 16, as shown in FIGS. 3a and 4d. Additionally, the beveled inner wall surface 66 aids the operator in guiding the porous end cap 72 of the product vial 18 as it is inserted into the proximal end section 64 of the applicator nozzle tip 16, as depicted in FIG. 4d.

Second Exemplary Embodiment 100

A second exemplary embodiment 100 of the present invention is illustrated in FIG. 2. Elements illustrated in FIG. 2 which correspond to the elements described above with reference to FIGS. 1, 3a to 4d have been designated by corresponding reference numbers increased by one hundred. The second embodiment 100 is constructed and operates in the same manner as the first embodiment 10, unless it is otherwise stated.

With reference to FIG. 2, the planar surface 126 of inner tray 114 does not include the lifting tab 44 or the finger grips 46 and 48 which are employed by the first embodiment 10. All of the other component parts of the second embodiment 100 are exactly the same as those of the first embodiment 10.

Third Exemplary Embodiment 200

A third exemplary embodiment 200 of the present invention is illustrated in FIGS. 5a and 5b. Elements illustrated in FIGS. 5a and 5b which correspond to the elements described above with reference to FIGS. 1, 3a to 4d have been designated by corresponding reference numbers increased by two hundred. The third embodiment 200 is constructed and operates in the same manner as the first embodiment 10, unless it is otherwise stated.

FIGS. 5a and 5b show an alternative applicator nozzle tip 216, which is detachably connected to the adhesive product vial 218. This embodiment 200 allows the nozzle tip 216 and the product vial 218 to be packaged (not shown) in a more conventional manner. More particularly, the nozzle tip 216 is detachably connected to the product vial 218 using a flexing connector assembly 280, which includes a flexible hinge member 282 having a first end 284, a center breakaway notch 285 and a second end 286. The flexing connector assembly 280 also includes a nozzle connector ring 288 integrally attached to the first end 284 of the hinge member 282 for connecting and attaching to the proximal end section 264 of the nozzle tip 216. The flexing connector assembly 280 further includes a vial connector ring 290 integrally attached to the second end 286 of the hinge member 282 for connecting and attaching to the distal end 270 of the product vial 218. The vial connector ring 290 includes a breakaway notch 292 located diametrically opposite the second end 286 of the hinge member 282.

With the use of the connector assembly 280, the operator can choose to utilize the attached nozzle connector ring 288 and the nozzle tip 216 to attach and join the nozzle tip 216 to the porous end cap 272 of the product vial 218, as depicted in FIG. 5b, or vice versa (i.e., the product vial 218 can be pivoted toward the end cap 272). The connector assembly 280 is now movably attached to both the nozzle tip 216 and product vial 218, such that the connector assembly 280 serves to prevent the product vial 218 from rolling while in the sterile field. If the operator chooses not to use the applicator nozzle tip 216, the attached nozzle connector ring 288 and the nozzle tip 216 may be separated from the overall connector assembly 280 by breaking and separating the connector assembly 280 at its breakaway notch 285. Alternatively, by severing the connector ring 290 at the breakaway notch 292, the entire connector assembly 280 can be separated and removed from the distal end section 270 of the adhesive vial 218. In yet another alternative configuration, in which the connector assembly 280 is separated at the center breakaway notch 285, the remainder of the connector assembly 280 that is in contact with the product vial 218 would serve to resist the rolling of the product vial 218 while in the sterile field. FIG. 5b can also represent a further alternate configuration in which the nozzle connector ring 288 and the nozzle tip 216 have a predetermined shape which is specifically selected so as to align the nozzle tip 216 with the product vial 218 for a more expedient assembly process and a more compact package.

Fourth Exemplary Embodiment 300

Figure 6A:
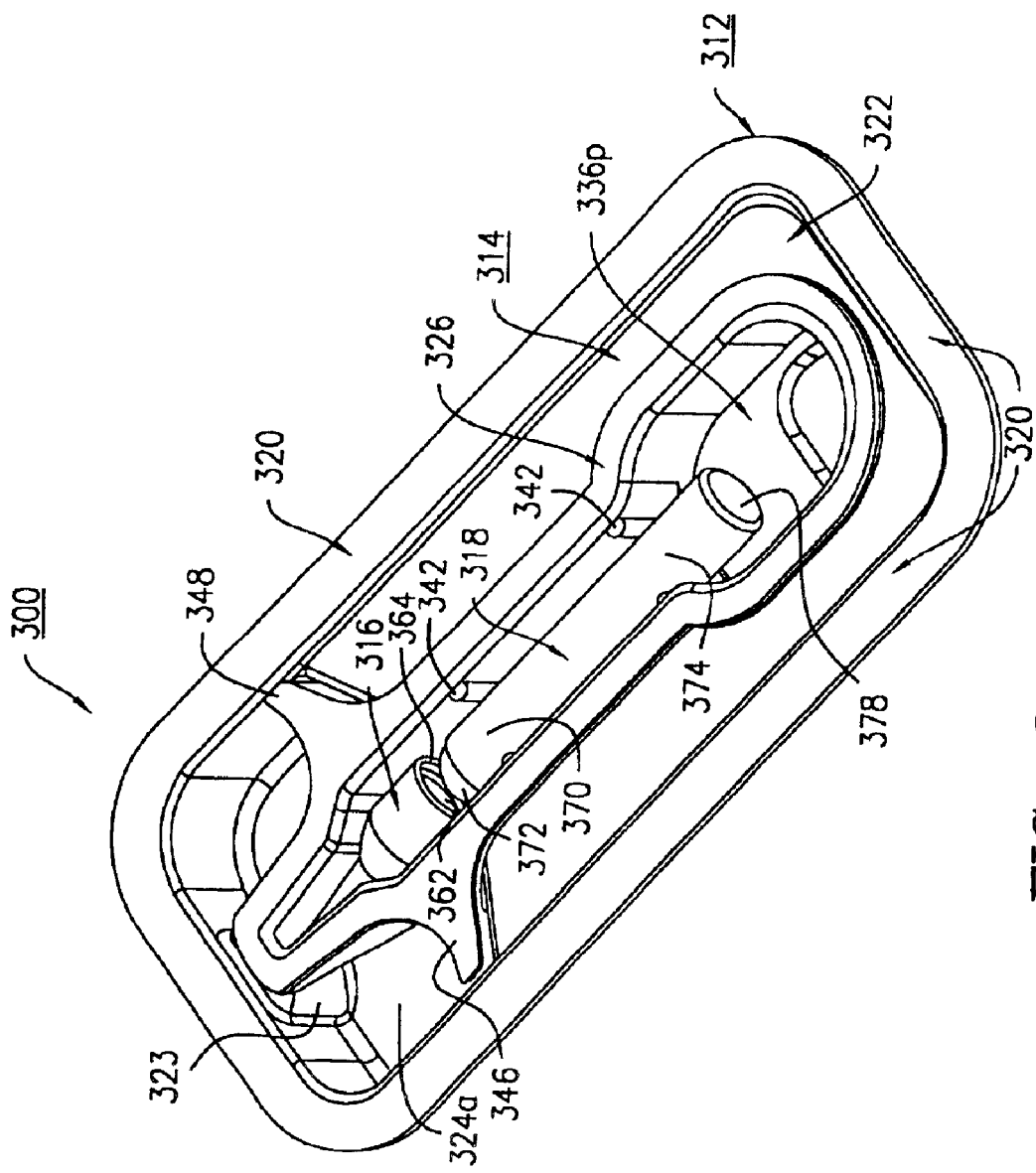
FIG. 6a is a top perspective view of a surgical adhesive package assembly constructed in accordance with a fourth exemplary embodiment of the present invention.
Figure 6B:
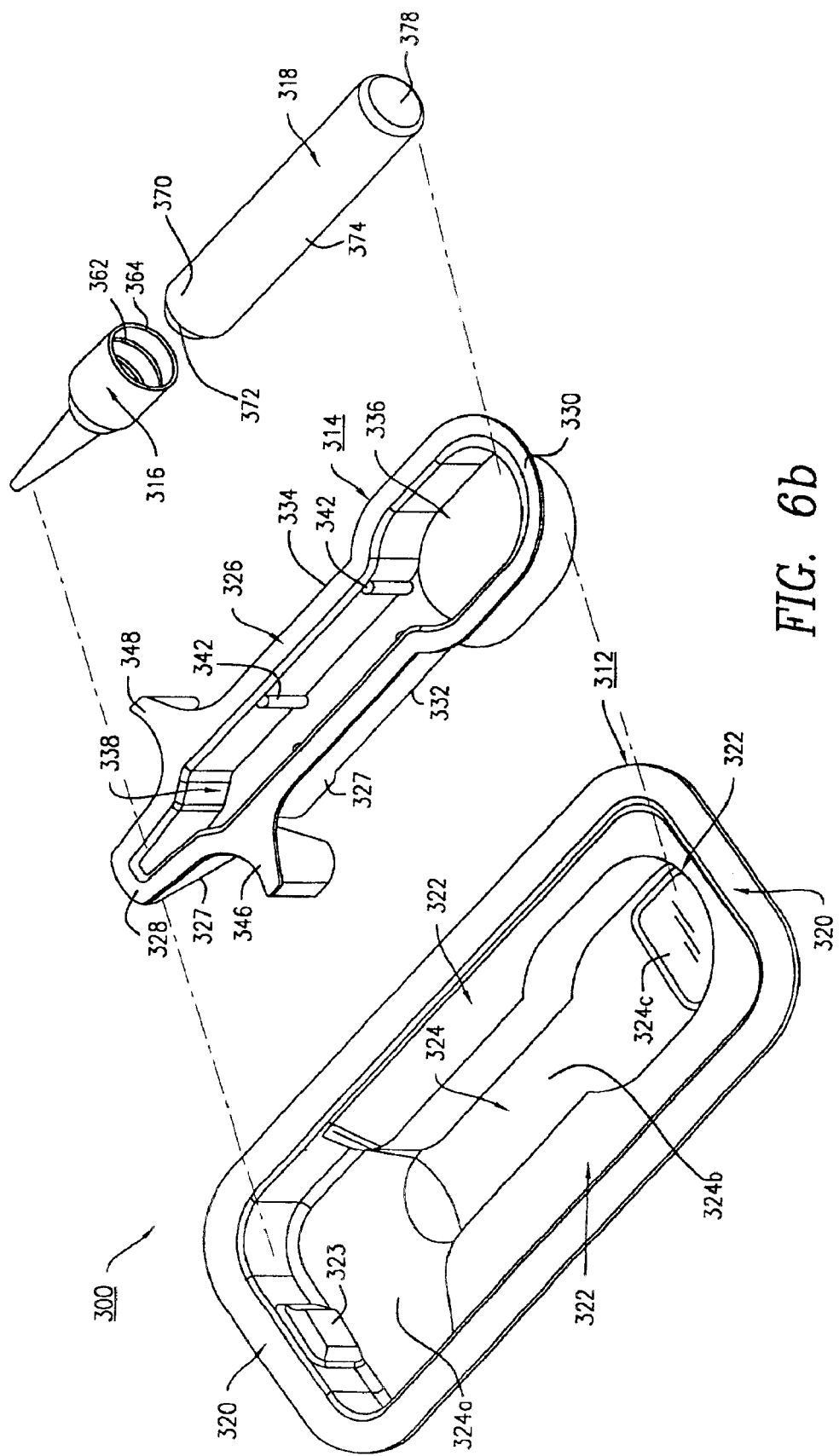

A fourth exemplary embodiment 300 of the present invention is illustrated in FIGS. 6a and 6b. Elements illustrated in FIGS. 6a and 6b which correspond to the elements described above with reference to FIGS. 1, 3a to 4d have been designated by corresponding reference numbers increased by three hundred. The fourth embodiment 300 is constructed and operates in the same manner as the first embodiment 10, unless it is otherwise stated.

The major differences between embodiment 300 and embodiment 10 are the size, design and configuration of the outer tray 312 and the inner tray 314, as compared with the outer tray 12 and the inner tray 14. More particularly, the outer tray 312 includes a partial inner perimeter ledge 322, stepped interior compartments 324a, 324b and 324c and a distal end tray rest 323 for receiving the distal end 328 of the inner tray 314. The inner tray 314 includes an opening 336, rather than a cavity, positioned adjacent to the proximal end 330 of the inner tray 314 for easier access to the product vial 318 when removing it from the inner tray 314, or when advancing it into the applicator nozzle tip 316. The inner tray 314 further includes enhanced finger rests/grips 346 and 348 which are shaped differently from the finger grips 46 and 48 of the first embodiment 10. Additionally, the inner tray 314 includes an enlarged flattened area 327 (at the side and bottom surfaces of the inner tray 314) for increased hand manipulation and comfort during assembly. The remaining component parts of embodiment 300 are substantially the same as their counterparts in the first embodiment 10.

Fifth Exemplary Embodiment 400

A fifth exemplary embodiment 400 of the present invention is illustrated in FIGS. 7a and 7b. Elements illustrated in FIGS. 7a and 7b which correspond to the elements described above with reference to FIGS. 1, 3a to 4d have been designated by corresponding reference numbers increased by four hundred. The fifth embodiment 400 is constructed and operates in the same manner as the first embodiment 10, unless it is otherwise stated.

The major differences between embodiment 400 and embodiment 10 are the size, shape and configuration of the outer tray 412 and the inner tray 414, as compared with the outer tray 12 and the inner tray 14. Further, this surgical package assembly 400 is used only for packaging the applicator nozzle tip 416 and does not therefore accommodate an adhesive product vial. The applicator nozzle tip 416 is located in a formed recessed cavity 438 (fitting the exact contours of the nozzle tip 416) within the inner tray 414. Additionally, the outer tray 412 includes a formed recessed compartment 424 (similar in size and shape to the formed recessed cavity 438 of inner tray 414) and a support section 425 located at a proximal end 421 of the outer perimeter rim 420. Support section 425 functions as a leg for maintaining the outer tray 412 in a level orientation.

The method for transferring the applicator nozzle tip 416 into a sterile field is similar to that described above. Thus, the inner tray 414 is flipped and turned-over into the sterile field by holding of the outer tray 412 by the user.

FIGS. 7a and 7b show only one nozzle tip 416 within the inner tray 414. In a modified embodiment, multiple applicator nozzle tips may be located within multiple recessed cavities of inner tray 414. To engage the applicator nozzle tip 416 over the porous end cap of a product vial (not shown), the operator simply advances the product vial towards and into the proximal end section 464 of the nozzle tip 416. Once the product vial is secured within the nozzle tip 416, the assembled combination may be removed from the recessed cavity 438 of inner tray 414 for use by the operator.

Sixth Exemplary Embodiment 500

A sixth exemplary embodiment 500 of the present invention is illustrated in FIGS. 8a and 8b. Elements illustrated in FIGS. 8a and 8b which correspond to the elements described above with reference to FIGS. 1, 3a to 4d have been designated by corresponding reference numbers increased by five hundred. The sixth embodiment 500 is constructed and operates in the same manner as the first embodiment 10, unless it is otherwise stated.

With reference to FIGS. 8a and 8b, the surgical adhesive packaging assembly 500 includes a tri-lobe housing 502 having a proximal end 503 and a distal end 504. The tri-lobe housing 502 includes three longitudinal cantilevered sections 505. These sections 505 serve to resiliently receive and align, along the longitudinal axis of the tri-lobe housing 502, the applicator nozzle tip 516 and the adhesive product vial 518. The three cantilevered sections 505 (three flattened surfaces) form an irregular outer contour 506 specifically designed to resist rolling of the tri-lobe housing 502 when placed on a surface in a sterile field. It should be noted that other contour designs that resist rolling are also contemplated within the scope of this embodiment.

The distal end 504 of the tri-lobe housing 502 includes a nozzle cavity section 538 for receiving the applicator nozzle tip 516 therein. The size and shape of the nozzle cavity section 538 are specifically selected so as to removably receive the nozzle tip 516. The nozzle cavity section 538 also includes a plurality of raised tabs 539 that, if and when employed, provide the nozzle cavity section 538 with the desired retention forces for holding the nozzle tip 516 in place. In this regard, the nozzle tip 516 is held in place with sufficient force to resist accidental dislodgement, but not so securely as to result in undue resistance to the removal of the combined applicator nozzle tip 516 and product vial 518 assembly, as shown in FIG. 8a, subsequent to the mounting sequence described hereinafter. In accordance with the aforementioned mounting sequence, the applicator nozzle tip 516 is inserted into the nozzle cavity section 538 of the tri-lobe housing 502 prior to the insertion of the adhesive product vial 518. The proximal end 503 of the tri-lobe housing 502 includes a vial compartment section 540 for receiving the adhesive product vial 518 therein. The size and shape of the vial compartment section 540 are specifically selected so as to removably receive the product vial 518 in place prior to use by the operator.

The tri-lobe housing 502 of the packaging assembly 500 may be molded from any number of suitable polymers using conventional molding equipment and processes. The applicator nozzle tip 516 and the adhesive product vial 518 may be provided as separate components within a secondary package assembly, such that the secondary package assembly may be fabricated from, for example, a TYVEK™ pouch. As with all embodiments, the internal components 516, 518 of any secondary packaging (e.g., TYVEK pouch) are sterilized so as not to contribute to a contamination problem when used in a sterile field. In use, the medical operator may pull back the secondary packaging assembly (not shown) and flip the nozzle tip 516 and the product vial 518 components onto a Mayo stand (not shown) within a sterile operating field. Once in the sterile field, another medical operator may choose to remove and use the adhesive product vial 518 with or without affixing the applicator nozzle tip 516 to the porous end cap 572 at the distal end 570 of the product vial 518. To affix the nozzle tip 516 to the distal end 570 of the adhesive product vial 518, the medical operator would simply push the product vial 518 towards the proximal end section 564 of the nozzle tip 516 until it firmly seats within the nozzle tip 516. The product vial 518 can then be removed with the applicator nozzle tip 516 firmly affixed thereto and ready for use.

Seventh Exemplary Embodiment 600

Figure 9B:
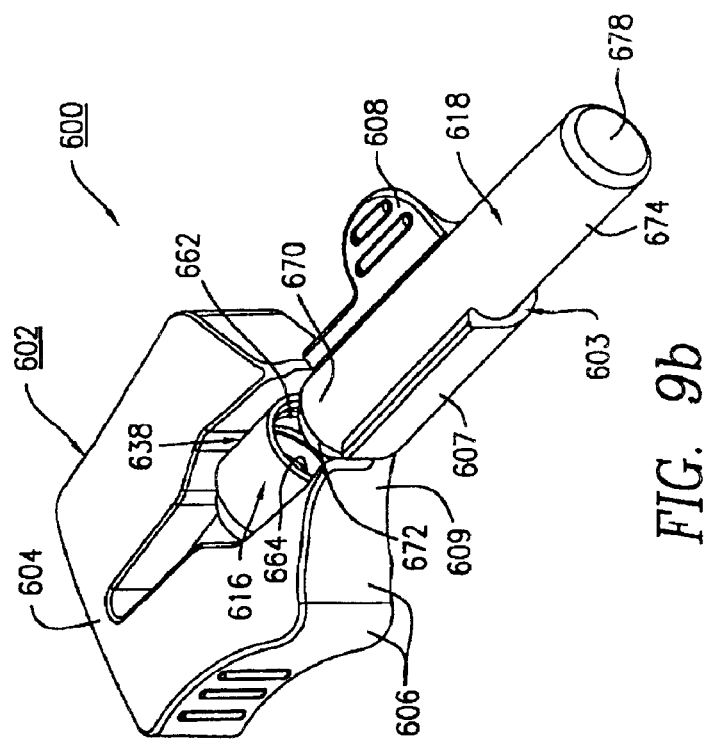
Figure 9A:
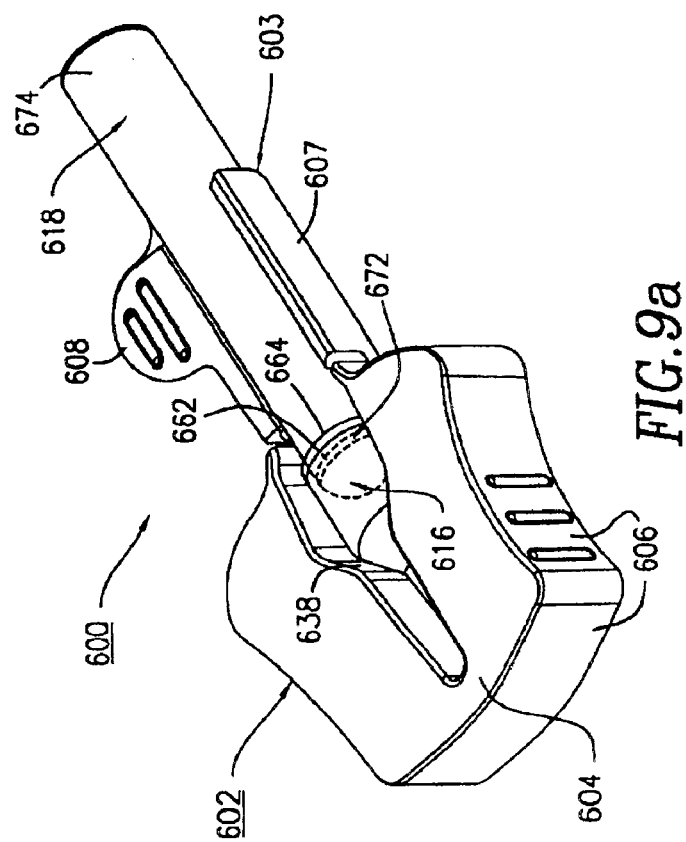
FIG. 9a is a front perspective view of a surgical adhesive package assembly constructed in accordance with a seventh exemplary embodiment of the present invention.
Figure 9C:
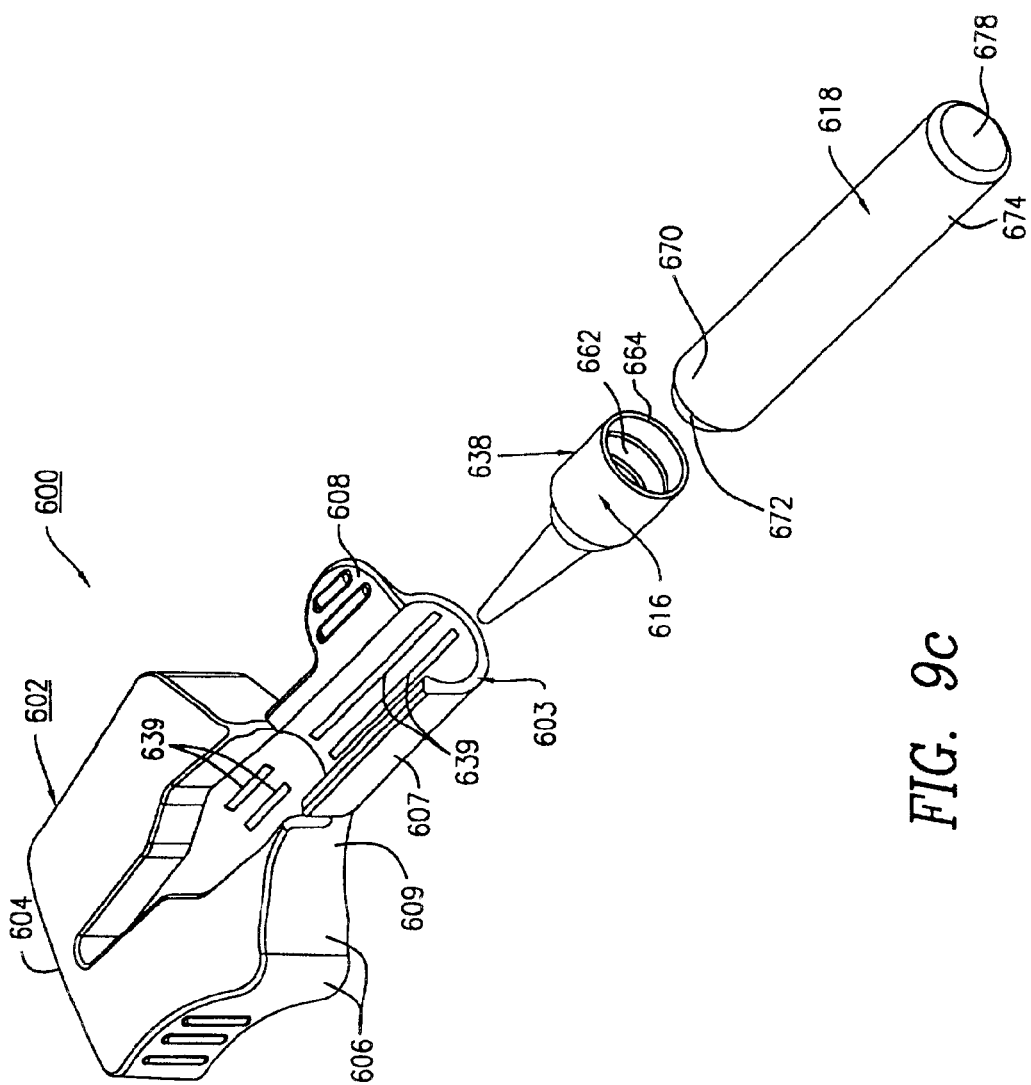
FIG. 9c is a rear exploded perspective view of the adhesive package assembly of FIG. 9b.

A seventh exemplary embodiment 600 of the present invention is illustrated in FIGS. 9a to 9c. Elements illustrated in FIGS. 9a to 9c which correspond to the elements described above with reference to FIGS. 1, 3a to 4d have been designated by corresponding reference numbers increased by six hundred. The seventh embodiment 600 is constructed and operates in the same manner as the first embodiment 10, unless it is otherwise stated.

Referring to FIGS. 9a to 9c, this embodiment, which is similar to the embodiment 500 in many respects, includes an overall structure adapted to assist in the removal of the combined applicator nozzle tip 616 and adhesive product vial 618 assembly from the surgical adhesive packaging assembly 600. More particularly, the surgical adhesive packaging assembly 600 includes an assembly housing 602 having a proximal end 603 and a distal end 604. The housing 602 is provided with an outer contour 606 adapted to resist rolling when the housing 602 is placed on a flat surface in a sterile field.

The distal end 604 of the housing 602 includes a nozzle cavity section 638 for receiving the applicator nozzle tip 616 therein. The size and shape of the nozzle cavity section 638 are specifically selected so as to removably receive the nozzle tip 616. The nozzle cavity section 638 also includes a plurality of raised tabs 639 that, if and when employed, provide the nozzle cavity section 638 with the desired retention forces for holding the nozzle tip 616 in place. More particularly, the nozzle tip 616 is held in place with sufficient force to resist accidental removal, but not so securely as to result in undue resistance to the removal of the combined applicator nozzle tip 616 and product vial 618 assembly, as shown in FIGS. 9a to 9c, subsequent to the mounting sequence described hereinafter. In accordance with the aforementioned mounting sequence, the applicator nozzle tip 616 is inserted into the nozzle cavity section 638 of housing 602 prior to the insertion of the adhesive product vial 618.

The proximal end 603 of housing 602 includes a cantilevered vial holding member 607 for receiving the adhesive product vial 618 therein. The width of the vial holding member 607 is specifically selected such that it is smaller than the diameter of the nozzle tip 616 and the diameter of the product vial 618, whereby the vial holding member 607 prevents the nozzle tip 616 and the product vial 618 from falling out or sliding out unless prompted to do so by the operator. The vial holding member 607 includes a wing member 608 for use in releasing the product vial 618 and/or the nozzle tip 616 from the vial holding member 607. When the operator applies pressure on the wing member 608 it further aids in the release of the product vial 618 with or without the nozzle tip 616.

The nozzle cavity section 638 and the vial holding member 607 also align and receive the nozzle tip 616 and the product vial 618 along a longitudinal axis of housing 602, as depicted in FIG. 9a. The vial holding member 607 is integrally and centrally attached to a rear wall 609 of housing 602, as shown in FIG. 9b. The general operational use of this embodiment 600 for dispensing into a sterile field and/or for affixing the nozzle tip 616 to the porous end cap 672 of the product vial 618 is almost exactly the same as that of the embodiment 500 of FIGS. 8a and 8b.

Eighth Exemplary Embodiment 700

An eighth exemplary embodiment 700 of the present invention is illustrated in FIGS. 10a, 10b, 10c and 10d. Elements illustrated in FIGS. 10a to 10d which correspond to the elements described above with reference to FIGS. 1, 3a to 4d have been designated by corresponding reference numbers increased by 700. The eighth embodiment is constructed and operates in the same manner as the first embodiment 10, unless it is otherwise stated.

Referring now to FIGS. 10a to 10d, this embodiment, which is similar to the embodiment 400 in many respects, and which incorporates certain features of the embodiments 500 and 600, is especially suitable for holding an applicator nozzle tip 716 without an adhesive product vial 718. As with the other embodiments, this packaging assembly 700 is intended to be sterile and packaged again within a secondary package assembly (i.e., having additional nozzle tips and/or product vials containing adhesives, etc.).

Figures 10A, 10B, 10C, 10D:
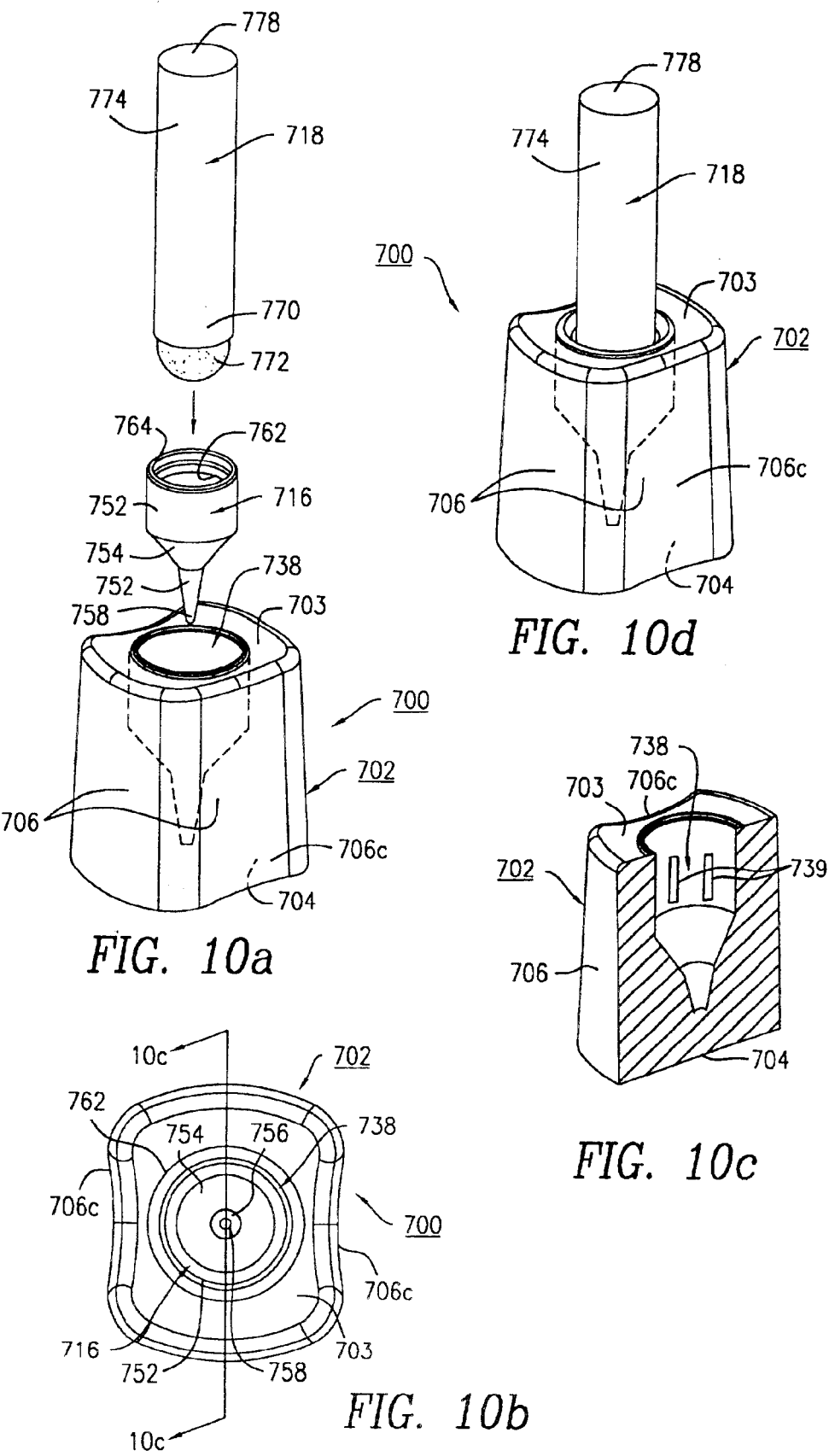
FIG. 10a is a top exploded perspective view of a surgical adhesive package assembly constructed in accordance with an eighth exemplary embodiment of the present invention.
FIG. 10b is a top plan view of the package assembly of FIG. 10a showing an applicator nozzle in a pre-loaded condition.
FIG. 10c is a cross-sectional view, taken along section line 10c—10c and looking in the direction of the arrows, of the package assembly of FIG. 10b without the nozzle tip.
FIG. 10d is a top perspective view of the package assembly of FIG. 10a illustrating its operational mode.

The packaging assembly 700 includes a tapered and cube-shaped housing 702 having a top end 703 (proximal side) and a bottom end 704 (distal side). The housing 702 is provided with an outer perimeter contour 706 specifically selected to resist rolling when the assembly housing 702 is placed on a flat surface in a sterile field. The housing 702 further includes a nozzle cavity section 738 centrally located and positioned towards the bottom end (distal side) 704 of the housing 702, as shown in FIGS. 10b and 10c, such that the applicator nozzle tip 716 is aligned along a longitudinal axis of the nozzle cavity section 738. The size and shape of the nozzle cavity section 738 are specifically selected so as to removably receive the applicator nozzle tip 716 therein. The nozzle cavity section 738 further includes a plurality of vertically extending raised tabs 739 adapted to provide the desired retention forces for holding the applicator nozzle tip 716 in place. More particularly, the nozzle tip 716 is held in place with sufficient force to resist accidental removal, but not so securely as to result in undue resistance to the removal of the combined applicator nozzle tip 716 and product vial 718 assembly, as shown in FIG. 10c, after the mounting sequence described hereinbelow. It should be noted that the housing 702 can be placed on one of its concave sides 706c on a flat surface or stood in an upright position, in which the bottom end 704 of assembly housing 702 can be placed on a flat surface for the operational use of the packaging assembly 700.

As previously mentioned, this packaging assembly 700 is designed and intended to only hold in place a single applicator nozzle tip 716. In accordance with the mounting sequence referred to above, the packaging assembly 700 (having already been pre-loaded with the nozzle tip 716) would be removed from the secondary packaging assembly when needed. An adhesive product vial 718 would already be available from other packaging assemblies. The operator would then take the distal end 770 of the product vial 718 and insert the porous end cap 772 at the distal end 770 of product vial 718 into the top end (proximal side) 703 of the housing 702 until the nozzle tip 716 is affixed to the product vial 718, as depicted in FIGS. 10a and 10d. Once the product vial 718 is firmly affixed to the nozzle tip 716, the combined product vial 718 and nozzle tip 716 assembly would be removed from the packaging assembly 700 in a condition ready for use by the operator.

It should be understood that the embodiments described herein are merely exemplary and that a person skilled in the art may make many variations and modifications without departing from the spirit and scope of the present invention. All such variations and modifications are intended to be included within the scope of the invention as defined in the appended claims.

What is claimed is:

1. A package, comprising a first product component; first holding means for releasably holding said first product component; a second product component; and second holding means for releasably holding said second product component such that said second product component is attachable to said first product component without removing either of said product components from said package, said first and second product components being movable relative to each other while they are held by said first and second holding means, respectively, said first holding means holding said first product component in a substantially fixed position relative to said package and said second holding means holding said second product component such that it is movable relative to said package between a first position, in which said second product component is detached from said first product component, and a second position, in which said second product component is attached to said first product component, whereby said first and second product components can be removed from the package as a unit.

2. A package according to claim 1, wherein said second holding means holds said second product component such that it is slidable from said first position to said second position.

3. A package according to claim 2, wherein said package includes a tray containing said first and second holding means, said tray having an exterior shape which inhibits it from rolling.

4. A package according to claim 3, wherein said tray is removably received within another tray.

5. A package according to claim 4, wherein said tray has means for permitting it to be gripped by a user and manually removed from said another tray.

6. A package according to claim 4, wherein said tray has means for permitting it to be held by a user as said second product component is slid from said first position to said second position.

7. A package according to claim 2, wherein said package includes a housing containing said first and second holding means, said housing having an exterior shape which inhibits it from rolling.

8. A package according to claim 7, wherein said first holding means holds said first product component such that it is entirely contained within said housing and said second holding means holds said second product component such that it is only partially contained within said housing.

* * * * *